United States Patent
Morgan

Patent Number: 6,146,587
Date of Patent: *Nov. 14, 2000

[54] SANITIZING DRY SPRAY MATERIAL AND APPLICATOR

[76] Inventor: David M. Morgan, 534 Rader Dr., Vandalia, Ohio 45377

[*] Notice: This patent issued on a continued prosecution application filed under 37 CFR 1.53(d), and is subject to the twenty year patent term provisions of 35 U.S.C. 154(a)(2).

[21] Appl. No.: 08/794,653

[22] Filed: Feb. 3, 1997

Related U.S. Application Data

[63] Continuation of application No. 08/399,149, Mar. 6, 1995, abandoned.

[51] Int. Cl.[7] .................................................. A01N 25/00
[52] U.S. Cl. ............................... 422/28; 422/1; 422/33; 424/45; 424/405; 514/642
[58] Field of Search .................................. 422/1, 28, 37, 422/32, 33; 424/45, 405; 514/642, 557; 222/635

[56] References Cited

U.S. PATENT DOCUMENTS

| | | | |
|---|---|---|---|
| H269 | 5/1987 | Malik | 422/37 |
| 3,169,905 | 2/1965 | Lambert | 422/28 |
| 3,364,068 | 1/1968 | Stern | 422/37 X |
| 3,445,564 | 5/1969 | Kirschner . | |
| 5,190,724 | 3/1993 | Hachmann et al. | 422/28 |
| 5,320,805 | 6/1994 | Kramer et al. | 422/28 |
| 5,336,424 | 8/1994 | Van Vlahakis et al. | 252/89.1 |

OTHER PUBLICATIONS

Ash, Michael and Irene, "Handbook of Cosmetic and Personal Care Additives", Gower Publishing Limited, p. 52, 1994.

*Primary Examiner*—Krisanne Thornton
*Attorney, Agent, or Firm*—Louis A. Scholz; David A. Greenlee

[57] ABSTRACT

The invention relates to toilet seat, body support, non food surface, disinfecting, cleaning and sanitizing by using a liquid cleaning or sanitizing solution, in general, and to provide a liquid for manual application, and alternatively for spray application; using a brush or disposable dispensing spray apparatus that permits an individual to quickly sanitize, or disinfect the surface, such as a toilet seat, which solution will rapidly dry or evaporate to allow almost immediate body part to body support non food surface contact use.

5 Claims, 1 Drawing Sheet

SANITIZING DRY SPRAY MATERIAL AND APPLICATOR

This is a Continuation of Ser. No. 08/399,149 filed Mar. 6, 1995 now abandoned.

FIELD OF THE INVENTION

The invention relates to surface cleaning or sanitizing by using spray cleaning or sanitizing aids, in general, and to provide a disposable dispensing spray apparatus that permits an individual to quickly use this spray to disinfect, and/or sanitize a surface, such as a toilet seat, and as a result of the rapid drying qualities of the mixture permitting the sanitizing solution dry or evaporate to allow prompt and comfortable bare skin or body part contact use.

BACKGROUND OF THE INVENTION

Historically individuals who have the need to use toilet or lavatory facilities, such as public rest rooms or rest rooms of others, are quite often apprehensive about using, or contacting with bare skin body parts, the toilet or lavatory seat, or examining table, surface generally provided. The reason, among others, that individuals quite often are apprehensive, is that there is a real or perceived danger of contacting a support surface that has been in prior use by others whose septic or aseptic condition is not known.

In some areas of the country and of the world, apparatus may be provided and available to supply a toilet seat shaped tissue paper cover to be placed over the toilet seat surface, prior to body part to toilet seat surface contact and use. Although helpful, those covers are of a basic, simplified substantially flat condition and of a general toilet seat outline and do not always adequately cover or completely protect the, bare body parts, contact with the seat area, in question, to satisfactorily protect the body part contact in use. In many places this above noted article is not provided, or available. Sometimes, this is caused by the cost that are involved to supply the toilet shaped tissue material and to install this material dispenser. Also involved are the costs and difficulty encountered to supply and maintain the material dispensing devices.

It is also well known, experienced, and appreciated, that one other practical process of addressing this problem, typically entails the relatively simple process of personally tearing various lengths of toilet paper from the standard toilet paper roll, or pack, in an attempt to fabricate a "cover" that will approximately correspond to the configuration of the toilet seat upper surface. While partially satisfactory in concept, the carrying out of such a plan of operation often suffers, as the laid out strips of paper do not readily remain in place, and thus may shift in position, both prior to and, or during use. Perhaps of greater importance, however, is that not all the public rest rooms or similar facilities offer toilet paper in rolls, but may provide folded, interleaved sheets. These individual sheets may then be positioned, one adjacent to the other, and placed around the toilet seat shape. Besides being tedious and cumbersome to arrange and difficult to retain the individual pieces in overlap position, this procedure is, often, time consuming, and quite probably even frustrating to carry out, and awkward in realization. It offers a physical barrier between that is of dubious continuity to provide protection for the person's body parts from the presumably contaminated seat surface. Also, unless paper is specially treated, the paper alone kills no germs.

As an alternative to the use of such protective devices, others have come forward to suggest that disinfecting or cleansing pads, such as shown in U.S. Pat. No. 5,025,524 be employed instead. These pads are to be pre-moistened with a germicidal or other cleansing agent, may be small enough to be easily carried about by the potential user. Alternatively the pads may be made readily available, or dispensed at the site to permit the user to physically wipe the surface of the toilet seat prior to its use. Suggestions abound as to specific formulations of the antiseptic solutions, and the substance of the carrier wiping material, with or without scenting, with various drying rates, with a variety of shelf lives prior to use, and with various kinds and degrees of antiseptic activity, such as taught in U.S. Pat. Nos. 5,093,031, and 5,028,458.

Some formulations of wiping material carriers are modified so as to be decomposable in water, so that they may be flushed away with the toilet waste. Prior art, such as U.S. Pat. No. 4,575,891 describes inter alia, for example, the advisability of incorporating alcoholic solutions, mercury zinc cyanide solutions, and other additives to effectuate rapid drying. These formulations and devices may not be sufficiently functional to disinfect the toilet seat in a single pass, but require repeated back-and-forth scrubbing actions to effectively distribute the germicidal solution to sanitize the entire seat surface. The entire upper, usually curved surface would be needed to be scrubbed by the germicidal solution to sanitize the contact area for body part contact protection, during use.

However, as can be seen, all of the above described devices, together or singly, have disadvantages over the herein disclosed user carried sanitizing "rapid dry" spray material and applicator. All of these prior art suggested devices require the individual to place his, or her, hand in contact, or at least in close proximity to the toilet seat surface, in order to effectuate cleaning or sanitizing operation, on the area that needs to be sanitized prior to use. Although the disclosed art may be effective, as to sanitizing; that operation leaves a "wet" uncomfortable, or unprotected toilet seat surface, which is undesirable.

A search of the art shows that there is no other sanitizing spray that has been designed for toilet seat surface personal protection, that leaves the seat, after application of an antiseptic material at a distance from the toilet seat surface, in a substantially uniform, clean, firm, dry, comfortable sanitized condition. The concept for this spray delivery system is to enable a person to easily spray a toilet seat surface, leaving a pleasant odor, and leaving a substantially dry, effectively, safely and continually surface sanitized toilet seat. No other sanitizing spray uses the same synergistically coacting formulation of ingredients; namely a concentrate of sanitizer together mixed into a combination of, an alcohol, such as ethanol, together with a propellant, such as isopentane, alone, or in combination with 152A-difluorethane. The use of this combination accomplishes the sanitizing of body contact surfaces, in a rapid or substantially immediate drying time. This combination of chemicals, produces a liquid carrier that dries or evaporates faster than alcohol alone.

DESCRIPTION OF THE PREFERRED EMBODIMENT

Figure 1:
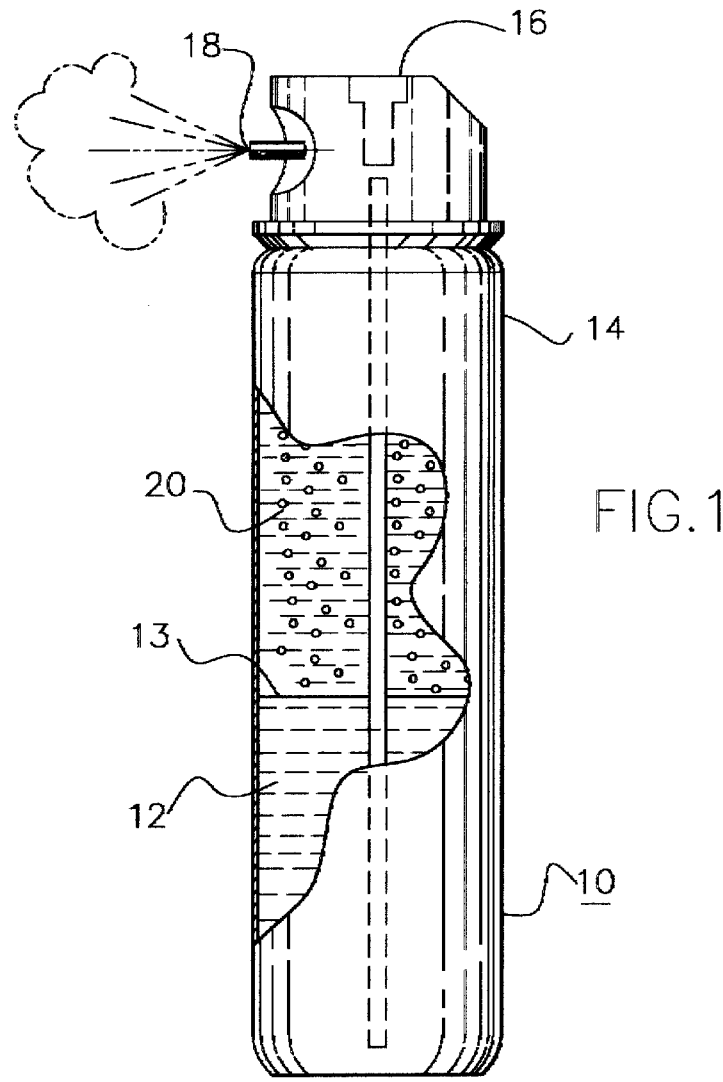
FIG. 1. Shows a partial phantom view of the solution container in the same elevation view, and additionally shows the stylized contents of the container, and the mechanism for spraying the inventive solution.
Figure 2:
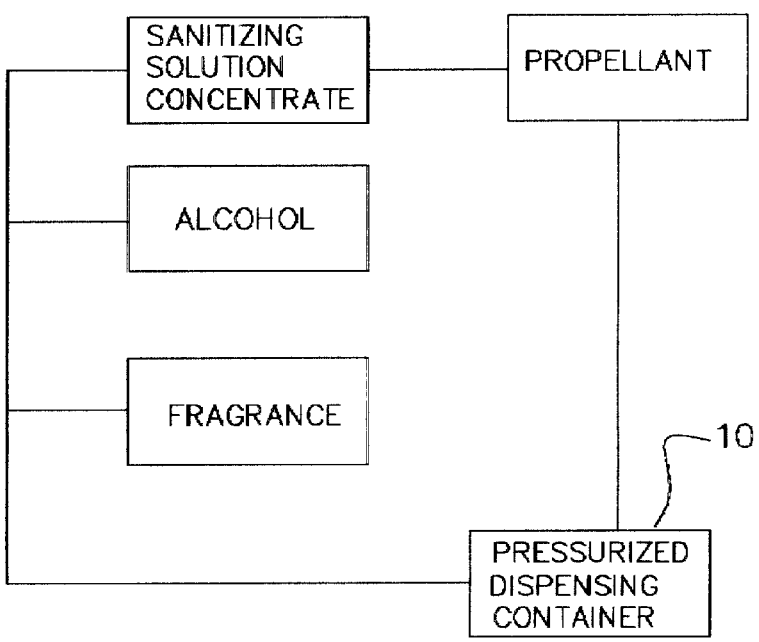
FIG. 2. Is a block diagram of the method of assembly and use of the subject material.

A sanitizer for, non food, contact surface sanitizing, is prepared and formulated, based on the uses and properties of a group of chemicals, broadly known as those based on n-decyl radical chlorides, of which a commercial form is represented by the chemicals marketed by the LONZA INC, CHEMICAL GROUP as BARDAC™ 2250 AND 2280.

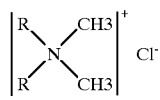

This class of chemical is described in the literature as didecyl dimethyl ammonium chloride, which is a germicidally active quaternary ammonium compound, capable of being miscible with a variety of propellant compounds.

An example of such a based mixture is shown as;

EXAMPLE I

In to One (1 Gal.) gallon of ethanol (denatured ethyl alcohol) is mixed, by adding 0.5 oz. of Bardac 2280 ( a quaternary ammonium compound) to one gallon of ethanol (using a ratio of 1:256). This combination can be blended, and is substantially almost as effective in all ratios from 50 parts per million, of an n-decyl radical chloride, to 4,000 parts per million; in an alcohol. This combination is then blended together until both are combined and commingled thoroughly and uniformly. At this time, a masking fragrance such as Dusty Rose; or other fragrance, of choice, is added 0.25 oz. to the 1 gallon of blend or mix until all ingredients including the ethanol and fragrance are thoroughly mixed to a consistent and uniform product. This portion is now called the "concentrate". One method of filling of the concentrate in to the dispenser is accomplished by filling through the top of the dispensing container 10, valve 16, using compressed carbon dioxide gas 20, to "push" or force the concentrate into the dispensing container.

The procedure, comprises, for example; a pressure container 14, container that is filled with 4 grams of the above referenced concentrate mixture to which is added the compressed gas or pentane, propane, or butane, as a propellant 20. A particular container may be one of approximately 17 ml. in volume which should be filled to about 38% shown at the surface of the liquid 13, by using the 4 grams of mixture or concentrate or liquid charge 12. The aerosol, or the propellant of choice, such as 152A difluorethane 30% by volume is used to fill to 80% of the container volume. The concentrate may be placed in the container ahead of the time before the propellant is inserted. At this point, concentrate and propellant have been added and the container is capped and ready. Such a size and formulation in the container 14 of the invention 10 will typically be able to spray propellant 20 and vaporized sanitizing vapor, thru pressure release valve 16, and spray nozzle 18, to sanitize about fifteen toilet seats.

EXAMPLE 2

One (1 Gal.) gallon of ethanol, is denatured by one of the many commonly known denaturing formulas such as; mixing by adding 6.0 oz. or 5% by volume of propyl alcohol, methyl, or other known denaturing agents, to the un-denatured ethyl alcohol, which now forms (denatured ethyl alcohol). To this (denatured ethyl alcohol), combination is added 0.5 oz. of Bardac 2280 (a quaternary ammonium compounds) to one gallon of the (denatured ethyl alcohol), ethanol and the germicidal active ingredient mixture is now called the "concentrate". The proportions of the differing alcohols can be varied widely according to the economic and functional considerations. The percentage of propellant to be added to the alcohols mixture may be changed increased or reduced. For example 40% of the concentrate can be added to 60% of the 152A difluorethane propellant to produce a workable mixture. However this mixture tends to have working pressures that are higher than desirable, from a safety and a cost and customer acceptance viewpoint.

EXAMPLE 3

Another mixture of 30% concentrate 50% isopentane and 20% 152A difluorethane, produces a more desirable, and economically desirable, having a lower container loading pressure, and thus a lighter walled D. O. T. (Department Of Transportation) rated container, and allows a more even and consistent spray over the life of the unit charge of the container. If the single propellant formula (Example 2 above) is used with the concentrate base, in the same proportions, a contrary result (i.e. a higher pressure is required to achieve the same spray results.) This higher pressure requires a thicker wall construction of the container, or the use of a higher strength alloy. These previously stated heavier requirements, result in greater expense to achieve the same spray results for the same delivered percentages of the main active ingredient.

Thus producing a liquid composition, rapid drying disinfecting and sanitizing solution, for spray application to hard non-food surfaces, consisting essentially of a homogenous mixture of at least two components, a sanitizing liquid selected from a group of quaternary ammonium compounds including one known as Bardac 2250, and one known as Bardac 2280, present in the percentage or at least 0.005% to 1.5%, mixed in with a second component consisting essentially of a rapid drying liquid selected from a group of liquid alcohols including ones known as denatured, propyl, methyl, and ethyl, of a consistency sufficient to be applied to the surface of a body supporting device.

To fill the container with a working mixture the concentrate may be added to the dispensing, by filling through the top of the dispensing container valve, using compressed carbon dioxide gas, or propellant to "push" or force the concentrate into the dispensing container. Alternatively the concentrate can be added to the un-crimped or un-capped container along with the propellant and then crimping or capping the container, before of after the valve is attached.

An example of charging, a 15 ml, to 17 ml, size container, is, that the charging container is filled with 4 grams of the above referenced concentrate mixture, to which is added the propellant such as compressed gas or pentane, propane, butane, or 152A difluorethane, and then capped. A particular container may be one of approximately 15 to 17 ml. in volume or larger or smaller, according to the use and application. It has been found that this size container typically allows a dozen or more applications of sanitizing material mixture to cover effectively, and sanitize, or germicidally clean a toilet seat surface, for each application. In a preferred fill the container should be filled to about 38% by volume by using 4 grams of mixture or concentrate. The sanitizer, is added to the propellant of choice, for example 30% of concentrate by volume is used to fill against 70% by compressed volume, of propellant or propellant mixture.

The concentrate may be placed in the container ahead of the time before the propellant is inserted. At this point, concentrate and propellant have been added and the container is capped and ready. Such a size and formulation will typically be able to spray and sanitize about fifteen toilet seats. The masking fragrance such as Dusty Rose, Strawberry, or Fresh Scent, can be purchased from Aroma Tech 197 Meister Ave Somerville N.J. 08876-3464:—(908) 707-0707.

The propellant may be (1) normal pentane (2) isopentane (3) normal butane (4) isobutane, (5) propane, any of which can be purchased from South Hampton Refining Co. Farm Road 418 P.O. Box 1636 Silsbe Tex. 77656, or 152A difluoroethane, 134 tetrachloroethane, and 227 A heptafluoropentane which can be purchased from Dupont. The 152A is preferred because it is politically correct and an environmentally friendly fluoro carbon producing no V O C's (Volatile Organic Carbons). The alcohol components, such as ethanols and the denatured alcohols, can be typically obtained from Laboratory Supply Co. in Louisville Ky.

I claim:

1. A sanitizing and disinfecting liquid composition suitable for use in an aerosol spray device, which contains a propellant, for the spray application of a thin, quick-drying film of said composition onto a surface subject to contact with human skin to sanitize and disinfect said surface, said composition consisting essentially of a didecyl dimethyl ammonium chloride germicidal agent in an alcohol diluent.

2. The composition of claim 1, wherein the germicidal agent is present in the alcohol in the ratio of from 50 to 4000 parts per million.

3. The composition of claim 2, wherein the alcohol is ethanol.

4. An aerosol spraying device, for the spray application of a thin, quick-drying film of sanitizing and disinfecting composition onto a surface, which is subject to contact with human skin, to sanitize and disinfect said surface, comprising a spray canister, a propellant, a sanitizing and disinfecting composition consisting essentially of a didecyl dimethyl ammonium chloride germicidal agent in an alcohol diluent, and a masking fragrance.

5. The device of claim 4, wherein the wherein the germicidal agent is present in the alcohol in the ratio of from 50 to 4000 parts per million.

* * * * *